United States Patent
Frommer

(10) Patent No.: US 6,245,970 B1
(45) Date of Patent: *Jun. 12, 2001

(54) DNA SEQUENCES FOR AN ARABIDOPSIS AMINO ACID TRANSPORTER, PLASMIDS, BACTERIA, YEASTS AND PLANTS CONTAINING A TRANSPORTER AND THEIR USE

(75) Inventor: Wolf-Bernd Frommer, Berlin (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/964,939

(22) Filed: Nov. 5, 1997

Related U.S. Application Data

(62) Division of application No. 08/362,512, filed as application No. PCT/EP93/01736 on Jul. 1, 1993, now Pat. No. 5,719,043.

(30) Foreign Application Priority Data

Jul. 5, 1992 (DE) .................................................. 42 22 315

(51) Int. Cl.[7] .............................. A01H 5/00; C12N 1/19; C12N 1/21; C12N 15/29; C12N 15/82
(52) U.S. Cl. .................. 800/298; 435/252.3; 435/254.2; 435/320.1; 435/468; 435/471; 536/23.6; 800/278; 800/286; 800/298
(58) Field of Search .................................. 536/23.6, 24.5; 435/172.3, 320.1, 252.3, 255.1, 419, 69.1, 468, 471, 254.2; 800/205, 278, 286, 298

(56) References Cited

U.S. PATENT DOCUMENTS 5,719,043 * 2/1998 Frommer .............................. 435/69.1

FOREIGN PATENT DOCUMENTS 4204103   8/1993 (DE) .

OTHER PUBLICATIONS

Li, Z.–C., et al., "Delta pH–Dependent Amino Acid Transport Into Plasma Membrane Vesicles Isolated From Sugar Beet Leaves", Plant Physiology, vol. 94, 1990, pp. 268–277.

Li, Z.–C., et al., "Delta pH–Dependent Amino Acid Transport Into Plasma Membrane Vesicles Isolated From Sugar Beet (Beta vulgaris L.) Leaves", Plant Physiology, vol. 96, 1991, pp. 1338–1344.

Tanaka, J., et al., "The Histidine Permease Gene "HIP1" of Saccharomyces Cerevisiae", Gene, vol. 38, 1985, pp. 205–214.

EMBL Sequence Database, Acc. No. X67124 Rel. 35, Feb. 28, 1993, A. Thaliana PPP mRNA for Amino Acid Permease I.

Frommer, W.B., et al., "Expression Cloning in Yeast of a cDNA Encoding Broad Specificity Amino Acid Permease from Arabidopsis Thaliana", Proceedings of the National Academy of Sciences of USA, vol. 90, Jul. 1, 1993, pp. 5944–5948.

Kwart et al. (1993) The Plant Journal, vol. 4, pp. 993–1002.*
Sentenac et al. (May 1, 1992) Science vol. 256, pp. 663–665.*
Ohniahl et al. (1980) Jpn. J. Gene, vol. 63, pp. 343–357.*
Oxender et al. (1980) Proc. Natl. Sci. USA vol. 77, pp. 1412–1416.*
Chen L, et al. "LHT1, a lysine—and histidine–specific amino acid transporter in Arabidopsis," Plant Physiol. 115: 1127–1134, 1997.*
Stam M, et al. "The silence of genes in transgenic plants," Ann. Bot. 79: 3–12, 1997.*
Koziel MG, et al. "Optimizing expression of transgenes with an emphasis on post–transcriptional events," Plant Mol. Biol. 32: 393–405, 1996.*
Smith CJS, et al. "Antisense RNA inhibition of polygalacturonase gene expression in transgenic tomatoes," Nature 334: 724–726, Aug. 25, 1988.*
Bush DR, et al. "Molecular analysis of plant sugar and amino acid transporters," J. Exp. Bot. 47: 1205–1210, Aug. 1996.*

* cited by examiner

Primary Examiner—Amy J. Nelson
(74) Attorney, Agent, or Firm—Frommer Lawrence & Haug LLP

(57) ABSTRACT

There are described DNA sequences from Arabidopsis that contain the coding region of amino acid transporters, as well as plasmids, bacteria, yeasts and plants containing these DNA sequences.

25 Claims, 5 Drawing Sheets

DNA SEQUENCES FOR AN ARABIDOPSIS AMINO ACID TRANSPORTER, PLASMIDS, BACTERIA, YEASTS AND PLANTS CONTAINING A TRANSPORTER AND THEIR USE

This application is a division of application Ser. No. 08/362,512, filed Jan. 5, 1995, now U.S. Pat. No. 5,719,043, which is a 371 of PCT/EP93/01736, designating the U.S. and filed Jul. 1, 1993.

BACKGROUND OF THE INVENTION 1. Field of the Invention

The present invention relates to DNA sequences that contain the coding region of amino acid transporters, whose introduction in a plant genome modifies the transfer of metabolites in transgenic plants, plasmids, bacteria, yeasts and plants containing these DNA sequences, as well as their use.

For many plant species it is known that the delivery of energy-rich compounds to the phloem through the cell wall takes place throughout the cell. Transporter molecules which allow the penetration of amino acids through the plant cell wall are not known.

In bacteria, numerous amino acid transport systems have been characterized. For aromatic amino acids, 5 different transporters have been described which can transport any one of phenylalanine, tyrosine and tryptophan, while the other transporters are specific for individual amino acids (see Sarsero et al., 1991, J Bacteriol 173: 3231–3234). The speed constants of the transport process indicates that the specific transport is less efficient. For several transporter proteins, the corresponding genes have been cloned. This has been achieved using transport-deficient mutants which were selected for their transport ability after transformation with DNA fragments as inserts in expression vectors (see Wallace et al., 1990, J Bacteriol 172: 3214–3220). The mutants were selected depending on their ability to grow in the presence of toxic analogues of amino acids, since the mutants cannot take these up and therefore cannot be impaired.

Corresponding complementation studies have been carried out with the eukaryotic yeast, *Saccharomyces cerevisiae*. Tanaka & Fink (1985, Gene 38: 205–214) describe a histidine transporter that was identified by complementation of a mutation. Vandenbol et al. (1989, Gene 83: 153–159) describe a proline transporter for *Saccharomyces cerevisiae*. The yeast possesses two different permeases for proline. One transports with lower efficiency and can be used also for other amino acids, and the other is proline-specific and works with high affinity. The latter was coded from the put4 gene. This carries an open reading frame for a peptide with a molecular weight of 69 kDa. The protein contains 12 membrane-penetrating regions, but does not contain any N-terminal signal sequence for secretion. This is a typical property of integral membrane proteins. The permeases process homology for arginine and for histidine permease from yeast, but not, however, for proline permease from *Escherichia coli*.

For plant cells, based on studies on tobacco suspension cultures, it has been found that the transport of arginine, asparagine, phenylalanine and histidine are pH and energy dependent. Since a 1,000-fold excess of leucine inhibits the transport of the other amino acids, it can be assumed, therefore, that all amino acids use the same transporter (McDaniel et al., 1982, Plant Physio 69: 246–249). Li and Bush (1991, Plant Physiol 96: 1338–1344) determined, for aliphatic, neutral amino acids, two transport systems in plasma membrane vesicles from *Beta vulgaris*. On the one hand, alanine, methionine, glutamine and leucine displace each other on the transporter protein. On the other hand, isoleucine, valine and threonine have mutually competitive effects. In combined competition kinetic studies (Li & Bush, 1990, Plant Physiol 94: 268–277) four different transport systems have been distinguished. Besides a transporter for all neutral amino acids, which work with low affinity, there exists a high affinity type which, however, possesses low affinity for isoleucine, threonine, valine and proline. Further transporters exist for acids as well as for basic amino acids.

The transporter molecule or gene for plant transporter proteins is not known.

SUMMARY OF THE INVENTION

There are now described DNA sequences which contain the coding region of a plant amino acid transporter, and whose information contained in the nucleotide sequence allows, by integration in a plant genome, the formation of RNA, by which a new amino acid transport activity can be introduced in the plant cells or an endogenous amino acid transporter activity can be expressed.

Under the term amino transporter is to be understood, for example a cDNA sequence that codes an amino transporter from *Arabidopsis thaliana*.

The identification of the coding region of the amino acid transporter is carried out by a process which allows the isolation of plant DNA sequences which code transporter molecules by means of expression in specific mutants of yeast *Saccharomyces cerevisiae*. For this, suitable yeast mutants have to be provided which cannot take up a substance for which the coding region of the transporter molecule has to be isolated from a plant gene library.

A mutant which cannot grow in media, with proline or citrulline as the only nitrogen source, is described by Jauniaux et al. (1987), Eur J Biochem 164: 601–606).

For the preparation of yeast strains that can be used to identify plant amino acid transporters, a yeast mutant which is not able to grow in media with proline and/or citrulline as the only nitrogen source is, for example, transformed with pFL 61 plasmid, which carries, as an insert, cDNA fragments from a cDNA library from *Arabidopsis thaliana*.

Further, a double mutant JT16 (Tanaka & Fink, 1985, Gene 38: 205–214) which has a deficiency in histidine synthesis (his4) and in histidine-uptake (hip1) is transformed with the described pFL 61 plasmid and cultivated in a medium with addition of histidine.

It has now surprisingly been found that, in the transformation of yeast cells, certain plant cDNA fragments can complement the yeast mutation. By analysis of the properties of the proteins coded from the cDNA it can be shown that a coding region that codes a plant amino acid transporter with a wide specificity spectrum is responsible for the complementing of the mutation (see example 3).

Such a coding region of an amino acid transporter is shown, for example, by one of the following nucleotide sequences:

1. Sequence (Seq. ID No. 1):

```
CTTAAAACAT TTATTTTATC TTCTTCTTGT TCTCTCTTTC TCTTTCTCTC ATCACT                56

ATG AAG AGT TTC AAC ACA GAA GGA CAC AAC CAC TCC ACG GCG GAA                 101
Met Lys Ser Phe Asn Thr Glu Gly His Asn His Ser Thr Ala Glu
1               5                   10                  15

TCC GGC GAT GCC TAC ACC GTG TCG GAC CCG ACA AAG AAC GTC GAT                 146
Ser Gly Asp Ala Tyr Thr Val Ser Asp Pro Thr Lys Asn Val Asp
                20                  25                  30

GAA GAT GGT CGA GAG AAG CGT ACC GGG ACG TGG CTT ACG GCG AGT                 191
Glu Asp Gly Arg Glu Lys Arg Thr Gly Thr Trp Leu Thr Ala Ser
            35                  40                  45

GCG CAT ATT ATC ACG GCG GTG ATA GGC TCC GGA GTG TTG TCT TTA                 236
Ala His Ile Ile Thr Ala Val Ile Gly Ser Gly Val Leu Ser Leu
                50                  55                  60

GCA TGG GCT ATA GCT CAG CTT GGT TGG ATC GCA GGG ACA TCG ATC                 281
Ala Trp Ala Ile Ala Gln Leu Gly Trp Ile Ala Gly Thr Ser Ile
                65                  70                  75

TTA CTC ATT TTC TCG TTC ATT ACT TAC TTC ACC TCC ACC ATG CTT                 326
Leu Leu Ile Phe Ser Phe Ile Thr Tyr Phe Thr Ser Thr Met Leu
                80                  85                  90

GCC GAT TGC TAC CGT GCG CCG GAT CCC GTC ACC GGA AAA CGG AAT                 371
Ala Asp Cys Tyr Arg Ala Pro Asp Pro Val Thr Gly Lys Arg Asn
                95                  100                 105

TAC ACT TAC ATG GAC GTT GTT CGA TCT TAC CTC GGT GGT AGG AAA                 416
Tyr Thr Tyr Met Asp Val Val Arg Ser Tyr Leu Gly Gly Arg Lys
                110                 115                 120

GTG CAG CTC TGT GGA GTG GCA CAA TAT GGG AAT CTG ATT GGG GTC                 461
Val Gln Leu Cys Gly Val Ala Gln Tyr Gly Asn Leu Ile Gly Val
                125                 130                 135

ACT GTT GGT TAC ACC ATC ACT GCT TCT ATT AGT TTG GTA GCG GTA                 506
Thr Val Gly Tyr Thr Ile Thr Ala Ser Ile Ser Leu Val Ala Val
                140                 145                 150

GGG AAA TCG AAC TGC TTC CAC GAT AAA GGG CAC ACT GCG GAT TGT                 551
Gly Lys Ser Asn Cys Phe His Asp Lys Gly His Thr Ala Asp Cys
                155                 160                 165

ACT ATA TCG AAT TAT CCG TAT ATG GCG GTT TTT GGT ATC ATT CAA                 596
Thr Ile Ser Asn Tyr Pro Tyr Met Ala Val Phe Gly Ile Ile Gln
                170                 175                 180

GTT ATT CTT AGC CAG ATC CCA AAT TTC CAC AAG CTC TCT TTT CTT                 641
Val Ile Leu Ser Gln Ile Pro Asn Phe His Lys Leu Ser Phe Leu
                185                 190                 195

TCC ATT ATG GCC GCA GTC ATG TCC TTT ACT TAT GCA ACT ATT GGA                 686
Ser Ile Met Ala Ala Val Met Ser Phe Thr Tyr Ala Thr Ile Gly
                200                 205                 210

ATC GGT CTA GCC ATC GCA ACC GTC GCA GGT GGG AAA GTG GGT AAG                 731
Ile Gly Leu Ala Ile Ala Thr Val Ala Gly Gly Lys Val Gly Lys
                215                 220                 225

ACG AGT ATG ACG GGC ACA GCG GTT GGA GTA GAT GTA ACC GCA GCT                 776
Thr Ser Met Thr Gly Thr Ala Val Gly Val Asp Val Thr Ala Ala
                230                 235                 240

CAA AAG ATA TGG AGA TCG TTT CAA GCG GTT GGG GAC ATA GCG TTC                 821
Gln Lys Ile Trp Arg Ser Phe Gln Ala Val Gly Asp Ile Ala Phe
                245                 250                 255

GCC TAT GCT TAT GCC ACG GTT CTC ATC GAG ATT CAG GAT ACA CTA                 866
Ala Tyr Ala Tyr Ala Thr Val Leu Ile Glu Ile Gln Asp Thr Leu
                260                 265                 270

AGA TCT AGC CCA GCT GAG AAC AAA GCC ATG AAA AGA GCA AGT CTT                 911
Arg Ser Ser Pro Ala Glu Asn Lys Ala Met Lys Arg Ala Ser Leu
                275                 280                 285
```

```
GTG GGA GTA TCA ACC ACC ACT TTT TTC TAC ATC TTA TGT GGA TGC        956
Val Gly Val Ser Thr Thr Thr Phe Phe Tyr Ile Leu Cys Gly Cys
                290                 295                 300

ATC GGC TAT GCT GCA TTT GGA AAC AAT GCC CCT GGA GAT TTC CTC       1001
Ile Gly Tyr Ala Ala Phe Gly Asn Asn Ala Pro Gly Asp Phe Leu
                305                 310                 315

ACA GAT TTC GGG TTT TTC GAG CCC TTT TGG CTC ATT GAC TTT GCA       1046
Thr Asp Phe Gly Phe Phe Glu Pro Phe Trp Leu Ile Asp Phe Ala
                320                 325                 330

AAC GCT TGC ATC GCT GTC CAC CTT ATT GGT GCC TAT CAG GTG TTC       1091
Asn Ala Cys Ile Ala Val His Leu Ile Gly Ala Tyr Gln Val Phe
                335                 340                 345

GCG CAG CCG ATA TTC CAG TTT GTT GAG AAA AAA TGC AAC AGA AAC       1136
Ala Gln Pro Ile Phe Gln Phe Val Glu Lys Lys Cys Asn Arg Asn
                350                 355                 360

TAT CCA GAC AAC AAG TTC ATC ACT TCT GAA TAT TCA GTA AAC GTA       1181
Tyr Pro Asp Asn Lys Phe Ile Thr Ser Glu Tyr Ser Val Asn Val
                365                 370                 375

CCT TTC CTT GGA AAA TTC AAC ATT AGC CTC TTC AGA TTG GTG TGG       1226
Pro Phe Leu Gly Lys Phe Asn Ile Ser Leu Phe Arg Leu Val Trp
                380                 385                 390

AGG ACC GCT TAT GTG GTT ATA ACC ACT GTT GTA GCT ATG ATA TTC       1271
Arg Thr Ala Tyr Val Val Ile Thr Thr Val Val Ala Met Ile Phe
                395                 400                 405

CTC TTC TTC AAC GCG ATC TTA GGT CTT ATC GGA GCA GCT TCC TTC       1316
Pro Phe Phe Asn Ala Ile Leu Gly Leu Ile Gly Ala Ala Ser Phe
                410                 415                 420

TGG CCT TTA ACG GTT TAT TTC CCT GTG GAG ATG CAC ATT GCA CAA       1361
Trp Pro Leu Thr Val Tyr Phe Pro Val Glu Met His Ile Ala Gln
                425                 430                 435

ACC AAG ATT AAG AAG TAC TCT GCT AGA TGG ATT GCG CTG AAA ACG       1406
Thr Lys Ile Lys Lys Tyr Ser Ala Arg Trp Ile Ala Leu Lys Thr
                440                 445                 450

ATG TGC TAT GTT TGC TTG ATC GTC TCG CTC TTA GCT GCA GCC GGA       1451
Met Cys Tyr Val Cys Leu Ile Val Ser Leu Leu Ala Ala Ala Gly
                455                 460                 465

TCC ATC GCA GGA CTT ATA AGT AGT GTC AAA ACC TAC AAG CCC TTC       1496
Ser Ile Ala Gly Leu Ile Ser Ser Val Lys Thr Tyr Lys Pro Phe
                470                 475                 480

CGG ACT ATG CAT GA TGAGTTTGAG ATCCTCAAGA GAGTCAAAAA              1541
Arg Thr Met His Glu
                485
TATATGTAGT AGTTTGGTCT TTCTGTTAAA CTATCTGGTG TCTAAATCCA           1591

ATGAGAATGC TTTATTGCTA AAACTTCATG AATCTCTCTG TATCTACATC           1641

TTTCAATCTA ATACATATGA GCTCTTCCAA AAAAAAAAAA AAAA                 1685
```

2. Sequence (Seq. ID No. 2):

```
                    CTATTTTAT AAATTCCTCTT CTTTTTTGTTC              29

ATAGCTTTGT AATTATAGTC TTATTTCTCT TTAAGGCTCA ATAAGAGGAG             79

ATG GGT GAA ACC GCT GCC GCC AAT AAC CAC CGT CAC CAC CAC CAT       124
Met Gly Glu Thr Ala Ala Ala Asn Asn His Arg His His His His
1               5                   10                  15

CAC GGC CAC CAG GTC TTT GAC GTG GCC AGC CAC GAT TTC GTC CCT       169
His Gly His Gln Val Phe Asp Val Ala Ser His Asp Phe Val Pro
                20                  25                  30

CCA CAA CCG GCT TTT AAA TGC TTC GAT GAT GAT GGC CGC CTC AAA       214
```

-continued

```
                    Pro Gln Pro Ala Phe Lys Cys Phe Asp Asp Asp Gly Arg Leu Lys
                                     35                  40                  45

AGA ACT GGG ACT GTT TGG ACC GCG AGC GCT CAT ATA ATA ACT GCG       259
Arg Thr Gly Thr Val Trp Thr Ala Ser Ala His Ile Ile Thr Ala
                 50                  55                  60

GTT ATC GGA TCC GGC GTT TTG TCA TTG GCG TGG GCG ATT GCA CAG       304
Val Ile Gly Ser Gly Val Leu Ser Leu Ala Trp Ala Ile Ala Gln
                 65                  70                  75

CTC GGA TGG ATC GCT GGC CCT GCT GTG ATG CTA TTG TTC TCT CTT       349
Leu Gly Trp Ile Ala Gly Pro Ala Val Met Leu Leu Phe Ser Leu
                 80                  85                  90

GTT ACT CTT TAC TCC TCC ACA CTT CTT AGC GAC TGC TAC AGA ACC       394
Val Thr Leu Tyr Ser Ser Thr Leu Leu Ser Asp Cys Tyr Arg Thr
                 95                 100                 105

GGC GAT GCA GTG TCT GGC AAC AGA AAC TAC ACT TAC ATG GAT GCC       439
Gly Asp Ala Val Ser Gly Asn Arg Asn Tyr Thr Tyr Met Asp Ala
                110                 115                 120

GTT CGA TCA ATT CTC GGT GGG TTC AAG TTC AAG ATT TGT GGG TTG       484
Val Arg Ser Ile Leu Gly Gly Phe Lys Phe Lys Ile Cys Gly Leu
                125                 130                 135

ATT CAA TAC TTG AAT CTC TTT GGT ATC GCA ATT GGA TAC ACG ATA       529
Ile Gln Tyr Leu Asn Leu Phe Gly Ile Ala Ile Gly Tyt Thr Ile
                140                 145                 150

GCA GCT TCC ATA AGC ATG ATG GCG ATC AAG AGA TCC AAC TGC TTC       574
Ala Ala Ser Ile Ser Met Met Ala Ile Lys Arg Ser Asn Cys Phe
                155                 160                 165

CAC AAG AGT GGA GGA AAA GAC CCA TGT CAC ATG TCC AGT AAT CCT       619
His Lys Ser Gly Gly Lys Asp Pro Cys His Met Ser Ser Asn Pro
                170                 175                 180

TAC ATG ATC GTA TTT GGT GTG GCA GAG ATC TTG CTC TCT CAG GTT       664
Tyr Met Ile Val Phe Gly Val Ala Glu Ile Leu Leu Ser Gln Val
                185                 190                 195

CCT GAT TTC GAT CAG ATT TGG TGG ATC TCC ATT GTT GCA GCT GTT       709
Pro Asp Phe Asp Gln Ile Trp Trp Ile Ser Ile Val Ala Ala Val
                200                 205                 210

ATG TCC TTC ACT TAC TCT GCC ATT GGT CTA GCT CTT GGA ATC GTT       754
Met Ser Phe Thr Tyr Ser Ala Ile Gly Leu Ala Leu Gly Ile Val
                215                 220                 225

CAA GTT GCA GCG AAT GGA GTT TTC AAA GGA AGT CTC ACT GGA ATA       799
Gln Val Ala Ala Asn Gly Val Phe Lys Gly Ser Leu Thr Gly Ile
                230                 235                 240

AGC ATC GGA ACA GTG ACT CAA ACA CAG AAG ATA TGG AGA ACC TTC       844
Ser Ile Gly Thr Val Thr Gln Thr Gln Lys Ile Trp Arg Thr Phe
                245                 250                 255

CAA GCA CTT GGA GAC ATT GCC TTT GCG TAC TCA TAC TCT GTT GTC       889
Gln Ala Leu Gly Asp Ile Ala Phe Ala Tyr Ser Tyr Ser Val Val
                260                 265                 270

CTA ATC GAG ATT CAG GAT ACT GTA AGA TCC CCA CCG GCG GAA TCG       934
Leu Ile Glu Ile Gln Asp Thr Val Arg Ser Pro Pro Ala Glu Ser
                275                 280                 285

AAA ACG ATG AAG AAA GCA ACA AAA ATC AGT ATT GCC GTC ACA ACT       979
Lys Thr Met Lys Lys Ala Thr Lys Ile Ser Ile Ala Val Thr Thr
                290                 295                 300

ATC TTC TAC ATG CTA TGT GGC TCA ATG GGT TAT GCC GCT TTT GGA      1024
Ile Phe Tyr Met Leu Cys Gly Ser Met Gly Tyr Ala Ala Phe Gly
                305                 310                 315

GAT GCA GCA CCG GGA AAC CTC CTC ACC GGT TTT GGA TTC TAC AAC      1069
Asp Ala Ala Pro Gly Asn Leu Leu Thr Gly Phe Gly Phe Tyr Asn
                320                 325                 330

CCG TTT TGG CTC CTT GAC ATA GCT AAC GCC GCC ATT GTT GTC CAC      1114
```

-continued

```
                    Pro Phe Trp Leu Leu Asp Ile Ala Asn Ala Ala Ile Val Val His
                                    335                 340                 345

CTC GTT GGA GCT TAC CAA GTC TTT GCT CAG CCC ATC TTT GCC TTT       1159
Leu Val Gly Ala Tyr Gln Val Phe Ala Gln Pro Ile Phe Ala Phe
                350                 355                 360

ATT GAA AAA TCA GTC GCA GAG AGA TAT CCA GAC AAT GAC TTC CTC       1204
Ile Glu Lys Ser Val Ala Glu Arg Tyr Pro Asp Asn Asp Phe Leu
                365                 370                 375

AGC AAG GAA TTT GAA ATC AGA ATC CCC GGA TTT AAG TCT CCT TAC       1249
Ser Lys Glu Phe Glu Ile Arg Ile Pro Gly Phe Lys Ser Pro Tyr
                380                 385                 390

AAA GTA AAC GTT TTC AGG ATG GTT TAC AGG AGT GGC TTT GTC GTT       1294
Lys Val Asn Val Phe Arg Met Val Tyr Arg Ser Gly Phe Val Val
                395                 400                 405

ACA ACC ACC GTG ATA TCG ATG CTG ATG CCG TTT TTT AAC GAC GTG       1339
Thr Thr Thr Val Ile Ser Met Leu Met Pro Phe Phe Asn Asp Val
                410                 415                 420

GTC GGG ATC TTA GGG GCG TTA GGG TTT TGG CCC TTG ACG GTT TAT       1384
Val Gly Ile Leu Gly Ala Leu Gly Phe Trp Pro Leu Thr Val Tyr
                425                 430                 435

TTT CCG GTG GAG ATG TAT ATT AAG CAG AGG AAG GTT GAG AAA TGG       1429
Phe Pro Val Glu Met Tyr Ile Lys Gln Arg Lys Val Glu Lys Trp
                440                 445                 450

AGC ACG AGA TGG GTG TGT TTA CAG ATG CTT AGT GTT GCT TGT CTT       1474
Ser Thr Arg Trp Val Cys Leu Gln Met Leu Ser Val Ala Cys Leu
                455                 460                 465

GTG ATC TCG GTG GTC GCC GGG GTT GGA TCA ATC GCC GGA GTG ATG       1519
Val Ile Ser Val Val Ala Gly Val Gly Ser Ile Ala Gly Ala Met
                470                 475                 480

CTT GAT CTT AAG GTC TAT AAG CCA TTC AAG TCT ACA TAT               1558
Leu Asp Leu Lys Val Tyr Lys Pro Phe Lys Ser Thr Tyr
                485                 490

TGATGATTAT GGACCATGAA CAACAGAGAG AGTTGGTGTG TAAAGTTTAC            1608

CATTTCAAAG AAAACTCCAA AAATGTGTAT ATTGTATGTT GTTCTCATTT            1658

CGTATGGTCT CATCTTTGTA ATAAAATTTA AAACTTATGT TATAAATTAT            1708

AAAAAAAAAA AAAAAAAAAA AAAAAAAAAA AA                               1740
```

The DNA sequences of the invention identified with the help of the transformed yeast strains, e.g., sequences Seq. No. 1 and 2, can be introduced into plasmids and thereby be combined with steering elements for expression in eukaryotic cells (see Example 4). These steering elements are, on the one hand, transcription promoters, and, on the other hand, transcription terminators. Plasmids can be used to transform eukaryotic cells with the aim of expression of a translatable mRNA which makes possible the synthesis of an amino acid transporter in the cells or with the aim of expression of a non-translatable RNA, which prevents synthesis of an endogenous amino acid transporter in the cells. The expression of an RNA corresponding to the inventive sequences of plant amino acid transporters modifies the plant acid metabolism, as well as total nitrogen metabolism. The economic significance of this modification is obvious. Nitrogen is the nutrient mainly responsible for limiting growth. The viability of germ lines as well as germination capacity of seeds is directly dependent on the nitrogen content of storage tissue. The formation of high value food materials with a high protein content is dependent on a sufficient nitrogen supply. Nitrogen is transported essentially in the form of amino acids. An improvement in the delivery of amino acids to their harvested parts can therefore lead to an increase in yield of agricultural plants. The possibility of forcing the uptake of amino acid in individual organs allows the qualitative improvement of such organs, which, because of the demands of the utilization process, contain little nitrogen. An example is potatoes which are grown for the production of starch. Besides this, it is possible to modify the whole plant, by which the growth of individual tissues, for example, leaves, is slowed down, while the growth of the harvested parts is increased. For this, one can imagine a lengthening of the vegetative phase of crops, which leads to an increased formation of storage substances.

Processes for the genetic modification of dicotyledonous and monocotyledonous plants are already known (see for example Gasser, C. S., Fraley, R. T., 1989, Science 244: 1293–1299; Potrykus, 191, Ann Rev Plant Mol Biol Plant Physiol 42: 205–225). For expression in plants the coding sequences must be coupled with the transcriptional regulatory elements. Such elements, called promoters, are known (EP 375091).

Further, the coding regions must be provided with transcription termination signals with which they can be correctly transcribed. Such elements are also described (see Gielen et al., 1989, EMBO J 8: 23–29). The transcriptional start region can be either native and/or homologous or foreign and/or heterologous to the host plant. If desired, termination regions are interchangeable with one another. The DNA sequence of the transcription starting and termination regions can be prepared synthetically, obtained naturally, or can be a mixture of synthetic and natural DNA constituents. For introduction of foreign genes in higher plants, a large number of cloning vectors are available that include a replication signal for *E. coli* and a marker which allows for the selection of the transformed cells. Examples of such vectors are pBR 322, pUC-Series, M13 mp-Series, pACYC 184, etc. Depending on the method of introduction of the desired gene in the plants, other DNA sequences may be suitable. Should the Ti- or Ri-plasmid be used, e.g., for the transformation of the plant cell, then at least the right boundary, often, however, both the right and left boundary of the Ti- and Ri-Plasmid T-DNA, is attached, as a flanking region, to the gene being introduced. The use of T-DNA for the transformation of plant cells has been intensively researched and is well described in EP 120 516; Hoekama, In: The Binary Plant Vector System, Offset-drukkerij Kanters B. V. Alblasserdam (1985), Chapter V; Fraley, et al., Crit. Rev. Plant Sci., 4:1–46 and An et al. (1985) EMBO J. 4: 277–287. Once the introduced DNA is integrate in the genome, it is generally stable there and remains in the offspring of the original transformed cells. It normally contains a selection marker which induces resistance in the transformed plant cells against a biocide or antibiotic such as kanamycin, G 418, bleomycin, hygromycin or phosphinotricin, etc. The individual marker employed should therefore allow the selection of transformed cells from cells which lack the introduced DNA.

For the introduction of DNA into a plant host cell, besides transformation using Agrobacteria, there are many other techniques available. These techniques include the fusion of protoplasts, microinjection of DNA and electroporation, as well as ballistic methods and virus infection. From the transformed plant material, whole plants can be regenerated in a suitable medium which contains antibiotics or biocides for selection. The resulting plants can then be tested for the presence of introduced DNA. No special demands are placed on the plasmids in injection and electroporation. Simple plasmids, such as, e.g., pUC-derivatives, can be used. Should whole plants be regenerated from such transformed cells, the presence of a selectable marker gene is necessary. The transformed cells grow within the plants in the usual manner (see also McCormick et al. (1986) Plant Cell Reports 5: 81–84). These plants can be grown normally and crossed with plants that possess the same transformed genes or different genes. The resulting hybrid individuals have the corresponding phenotypical properties.

The DNA sequences of the invention can also be introduced in plasmids and thereby combined with steering elements for an expression in prokaryotic cells. The formation of a translatable RNA sequence of a eukaryotic amino acid transporter from bacteria, in spite of the considerable differences in the membrane structures of prokaryotes and eukaryotes, means that prokaryotes can now use a eukaryotic amino acid transporter with specificity for certain substrates. This makes possible the production of bacterial strains which could be used for studies of the properties of the transporter as well as its substrate.

The invention also relates to bacteria that contain the plasmids of the invention.

The DNA sequences of the invention can also be introduced in plasmids which allow mutagenesis or a sequence modification through recombination of DNA sequences in prokaryotic or eukaryotic systems. In this way, the specificity of the amino acid transporter can be modified. Thus, the specificity of the transporter can be changed.

The invention also relates to derivatives or parts of plasmids that contain the DNA sequences of the invention and which can be used for the transformation of prokaryotic and eukaryotic cells.

By using standard processes (see Sambrook et al., 1989, Molecular Cloning: A Laboratory Manual, 2d ed., Cold Spring Harbor Laboratory Press, NY, USA), base exchanges can be carried out or natural or synthetic sequences can be added. For binding DNA fragments with one another, adaptors or linkers can be introduced on the fragments. Further, manipulations can be carried which prepare suitable restriction cleavage sites or remove the excess DNA or restriction cleavage sites. Where insertions, deletions or substitutions such as, for example, transitions and transversions are desired, in vitro mutagenesis, primer repair, restrictions or ligations can be used. For methods of analysis, in general, a sequence analysis, restriction analysis and other biochemical molecular biological methods can be used. After each manipulation, the DNA sequence used can be cleaved and bound with another DNA sequence. Each plasmid sequence can be cloned in the same or different plasmids.

Derivatives or parts of the DNA sequences and plasmids of the invention can also be used for the transformation of prokaryotic and eukaryotic cells. Further, the DNA sequences of the invention can be used according to standard processes for the isolation of similar sequences on the genome of plants of various species, which also code for amino acid or other oligosaccharide transporter molecules. With these sequence constructs, for the transformation of plant cells, can be prepared which modify the transport process in transgenic plants.

In order to specify related DNA sequences, gene libraries must first be prepared which are representative of the content of genes of a plant type or for the expression of genes in a plant type. The former are genomic libraries, while the latter are cDNA libraries. From these, related sequences can be isolated using the DNA sequences of the invention as probes. Once the related gene has been identified and isolated, a determination of the sequence and an analysis of the properties of the proteins coded from this sequence is possible.

In order to understand the examples forming the basis of this invention all the processes necessary for these tests and which are known per se will first of all be listed:

1. Cloning Process

For cloning in *E. coli*, the vector pBluescriptSK (Short et al., 1988, Nucl Acids Res 16: 7583–7600) was used.

For the transformation of yeasts, the vector pFL61 (Minet & Lacroute, 1990, Curr Genet 18: 287–291) was used.

For the plant transformation the gene constructs in the binary vector pBIN-Hyg were cloned. 2. Bacterial and Yeast Strains For the pBluescriptSK vector as well as for PBinAR constructs, the *E. coli* strain XL1blue (Bullock et al., 1987, Biotechniques, 5, 376–378) was used.

As a starting strain for the expression of the cDNA library in yeast, the yeast strain 22574d (Jauniaux et al., 1987 Eur J Biochem 164: 601–606) was used.

The transformation of the plasmids in potato plants was carried out using *Agrobacterium tumefaciens* strain LBA4404 (Bevan (1984) Nucl. Acids Res 12: 8711–8720).

3. Transformation of *Agrobacterium tumefaciens*

The transfer of the DNA in Agrobacteria was carried out by direct transformation by the method of Höfgen & Willmitzer (1988, Nucleic Acids Res 16: 9877). The plasmid DNA of the transformed Agrobacterium was isolated in accordance with the method of Birnboim and Doly (1979) (Nucl Acids Res 7: 1513–1523) and was analyzed by gel electrophoresis after suitable restriction cleavage.

4. Plant Transformation

Ten small leaves, wounded with a scalpel, of a sterile potato culture were placed in 10 ml of MS medium with 2% amino acid containing 30–50 μl of an *Agrobacterium tumefaciens* overnight culture grown under selection. After 3–5 minutes of gentle shaking, the leaves were laid out on MS medium of 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% bacto agar. After incubation for one week at 25° C. and 3000 lux, the claforan concentration in the medium was reduced by half.

Deposits

The following plasmids and yeast strains were deposited at the Deutschen Sammlung von Mikroorganismen (DSM) in Braunschweig, Germany on 12.06.1992 (deposit number):

| Plasmid | pPPP1-20 | (DSM 7129) |
| Plasmid | pBinPPP1-20 | (DSM 7130) |

Other features and advantages of the present invention will become apparent from the following description of the invention which refers to the accompanying drawings.

no=time period of the uptake without competitor;

proline=time period with fourfold excess of unlabeled proline;

citrulline=time period with fourfold excess of unlabeled citrulline;

GABA=time period with fourfold excess of gamma-aminobutyric acid;

time=time in seconds;

cpm=decays counted per minute.

Figure 3:
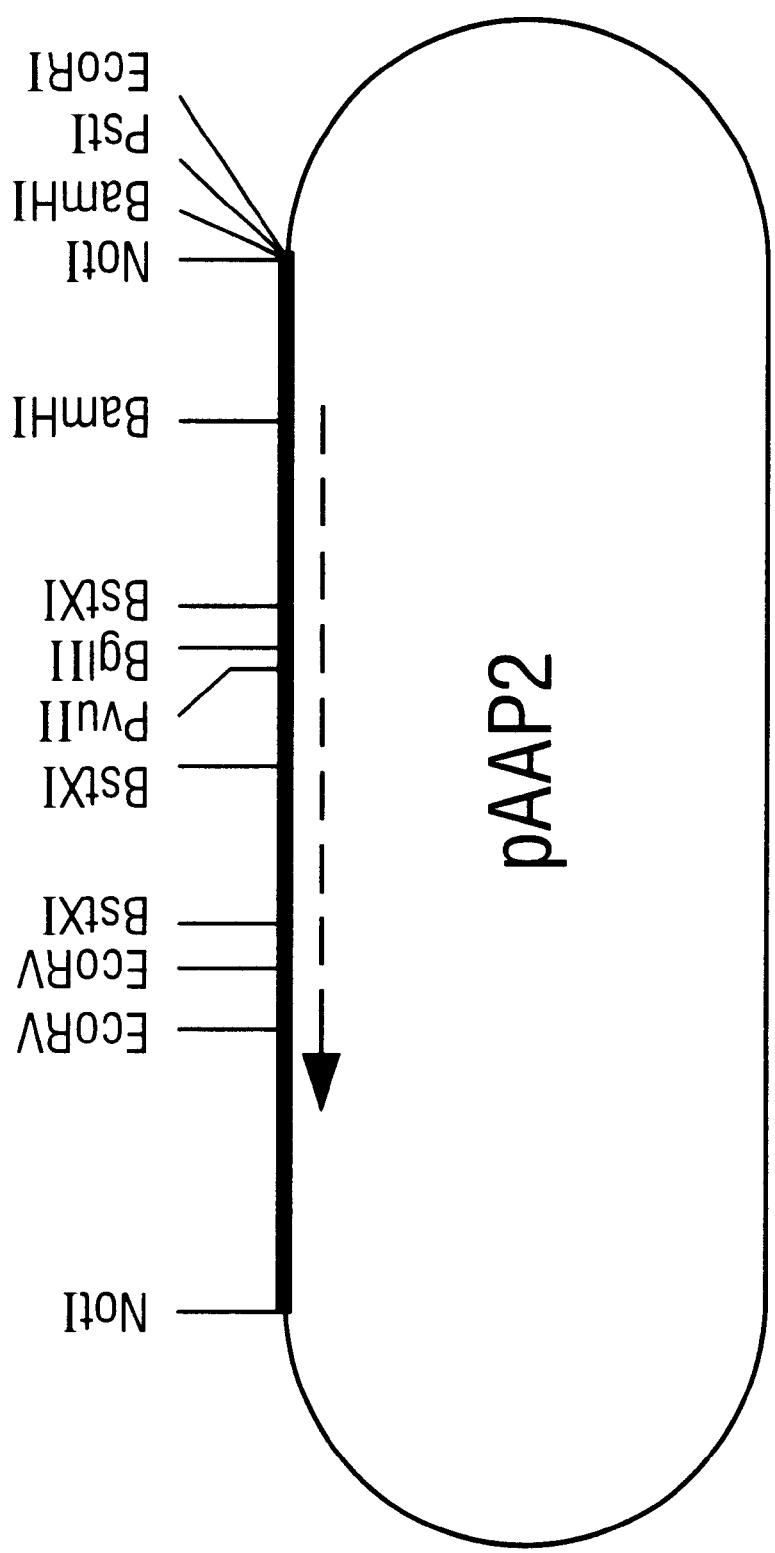

FIG. 3 shows the plasmid pAAP2 which contains the sequence Seq-ID No. 2. The finely drawn line corresponds to the sequence from pBluescriptSK. The thicker line represents the cDNA insert. The cleavage positions of the inserts are shown.

Figure 4:
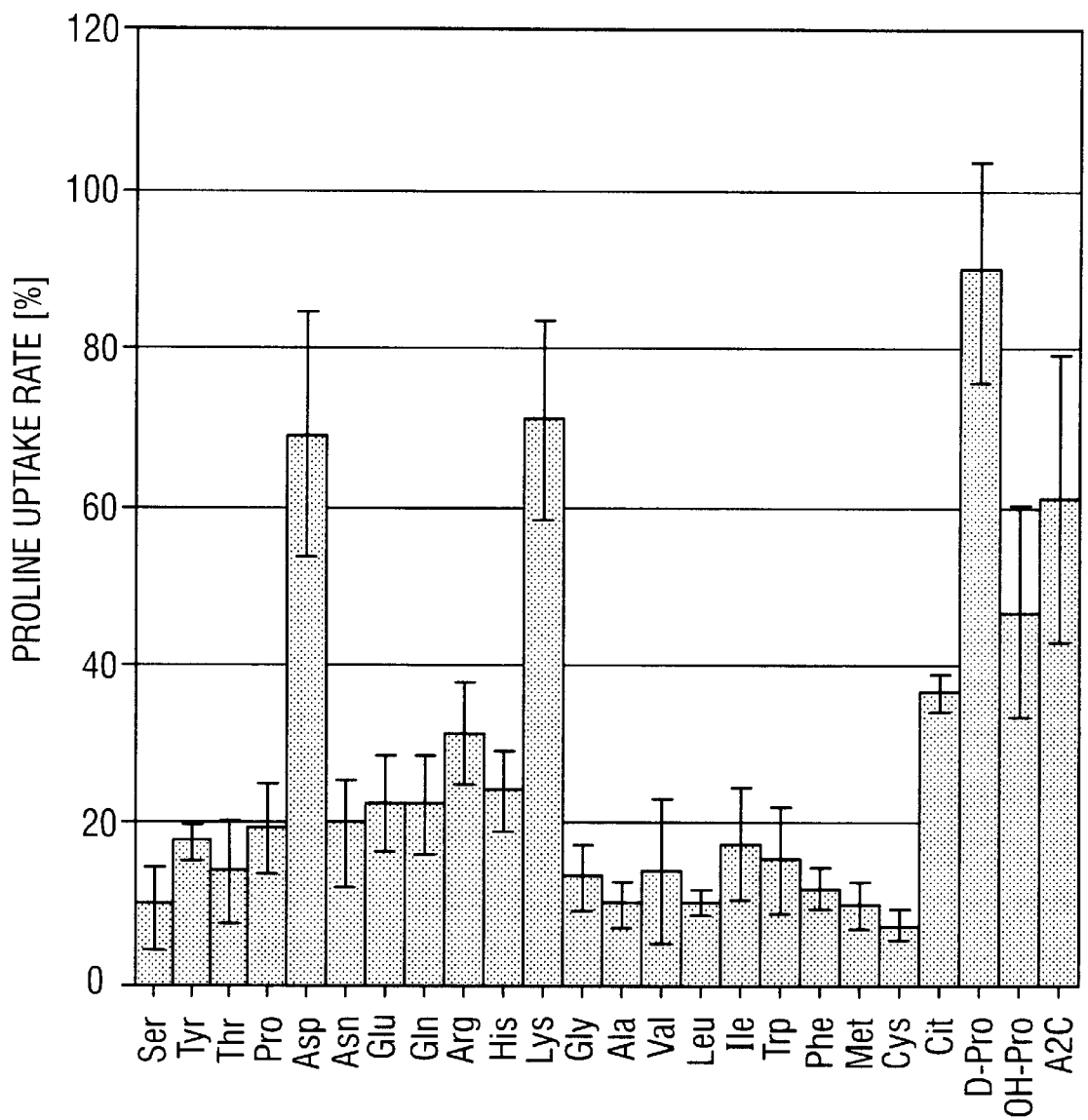

FIG. 4 shows a competition experiment with the yeast line 22574d::AAP2. In this experiment, the uptake of $^{14}$C-labeled L-proline from the medium in the presence of a fourfold excess of other amino acids or their analogues is measured. Besides the standard abbreviations for amino acids in the three letter code, the following are also used:

Cit=citrulline;

D-Pro=D-proline;

OH-Pro=hydroxyproline; and

AC2=azetidine-2-carboxylic acid.

Figure 5:
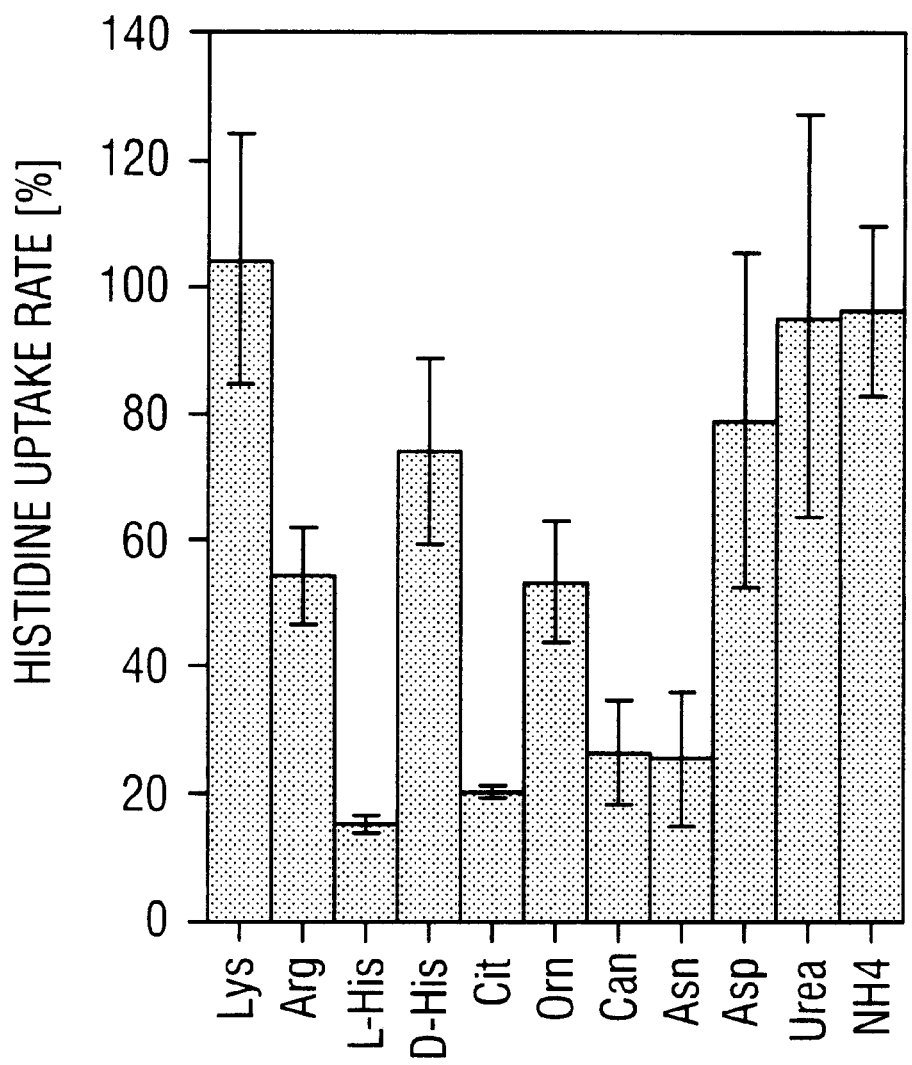

FIG. 5 shows a competition experiment with the yeast line JT16::AAP2. In this experiment, the uptake of $^{14}$C labeled L-histidine from the medium in the presence of a tenfold excess of other amino acids or their analogues is measured.

Besides the standard abbreviations for amino acids in the three letter code, the following are also used:

Cit=citrulline;

Orn=ornithine;

Can=canavanine; and

NH4=ammonium.

DETAILED DESCRIPTION OF THE PREFERRED EMBODIMENTS

The following examples describe the cloning and identification, as well as the function and use of a plant amino acid transporter.

EXAMPLE 1

Cloning of the cDNA of a Plant Amino Acid Transporter

For complementation of the proline transport mutation of the yeast strain 22574d (Jauniaux et al., 1987, Eur J Biochem 164: 601–606) and/or the histidine synthesis and transport mutation of the strain JT16 (Tanaka & Fink 1985, Gene 38: 205–214), a cDNA of young germ lines from *Arabidopsis thaliana* (two leaf stage) in the yeast expression vector pFL61 (Minet & Lacroute), 1990 Curr Genet 18: 287–291) which had been made available by Minet (Minet et al., 1992, Plant J 2: 417–422) was used. Around 1 μg of the vector with the CDNA-insert was transformed in the yeast strain 22574d and/or JT16 by the method of Dohmen et al. (1991, Yeast 7: 691–692). Yeast transformants, which could grow in media with 4 mM proline as the sole nitrogen source or in media with 6 mM histidine, were propagated. From the lines plasmid-DNA was prepared by standard methods. Clones that could complement the particular mutation contained plasmids with similar restriction type of the CDNA insert. These varied in size between 1.6 and 1.7 kb.

EXAMPLE 2

Sequence Analysis of the CDNA Insert of the Plasmid pFL61-ppp1-20

Figure 1:
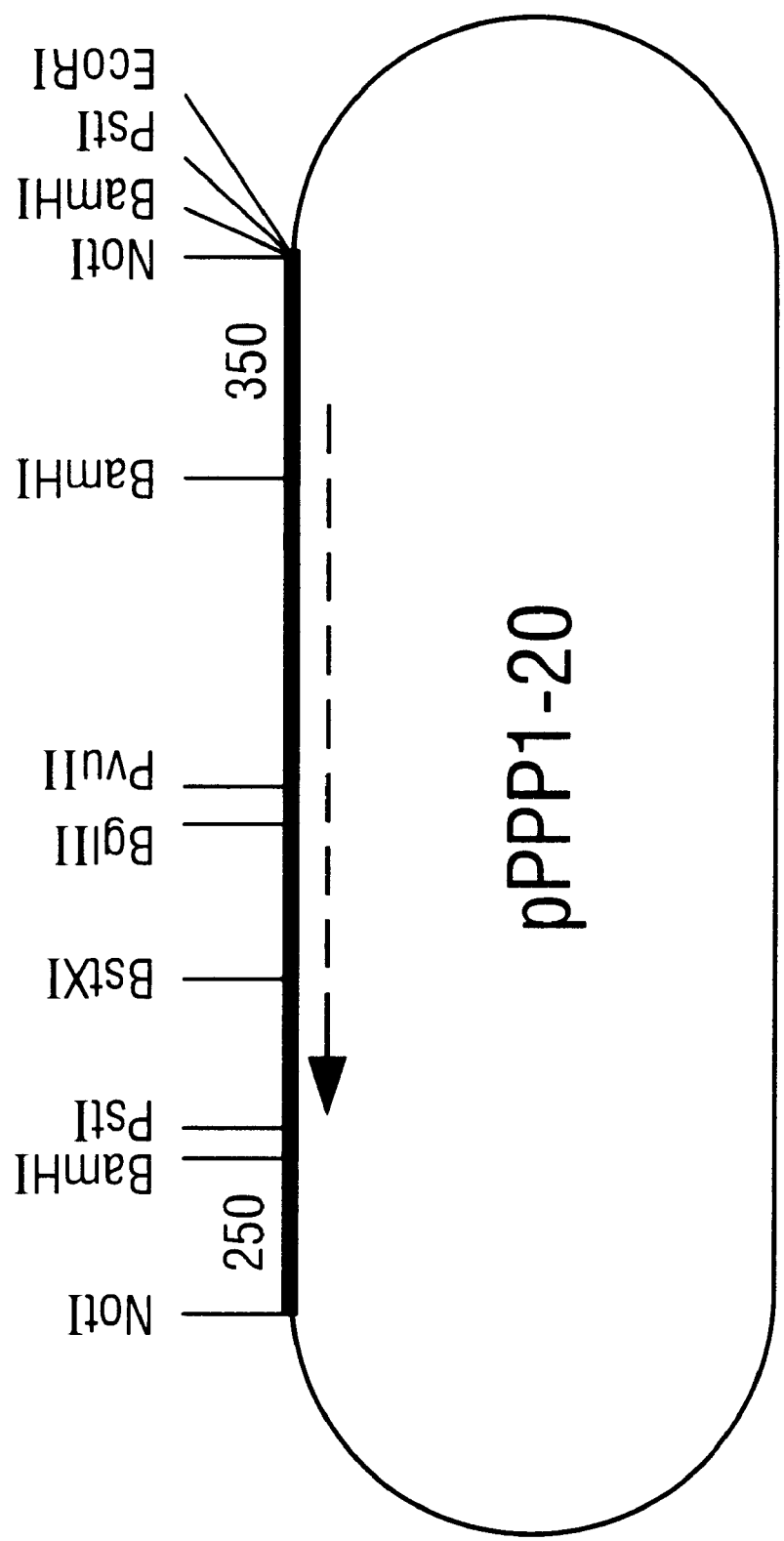
FIG. 1 shows the plasmid pPPP1-20 which contains the sequence Seq-ID No. 1. The finely drawn line corresponds to the sequence from pBluescriptSK. The thicker line represents the CDNA insert. The cleavage positions of the inserts are shown.

From a yeast line PPP1-20, obtained in a similar manner to example 1, which, in spite of the 22574d mutation, could grow with proline as the only nitrogen source, the plasmid pFL61-ppp1-20 was isolated. Its cDNA insert was prepared as a NotI fragment and cloned in the vector pBluescriptSK. In this way, the plasmid pPPP1-20 was obtained (see FIG. 1). Using synthetic oligonucleotides, the insert was sequenced by the method of Sanger et al. (1977, Proc Natl Acad Sci USA 74:5463–5467). The sequence is given above (SEQ ID No. 1).

In a similar way, from a yeast line that, in spite of the his4/hip1 double mutation, could be grown in a medium with histidine addition, the plasmid pFL61-aap2 was isolated whose insert was also cloned as a NotI fragment in pBluescriptSK. The resulting plasmid pAAP2 was sequenced and the sequence (SEQ ID No. 2) is given above. The plasmid pAAP2 has a similar structure to pPPP1-20 (see FIG. 1), but instead of the insert SEQ ID No. 1, carries the insert SEQ ID No. 2 (see FIG. 3).

EXAMPLE 3

Uptake Studies with $^{14}$C-labeled Protein into the Yeast Line PPP1-20 and AAP2

Figure 2:
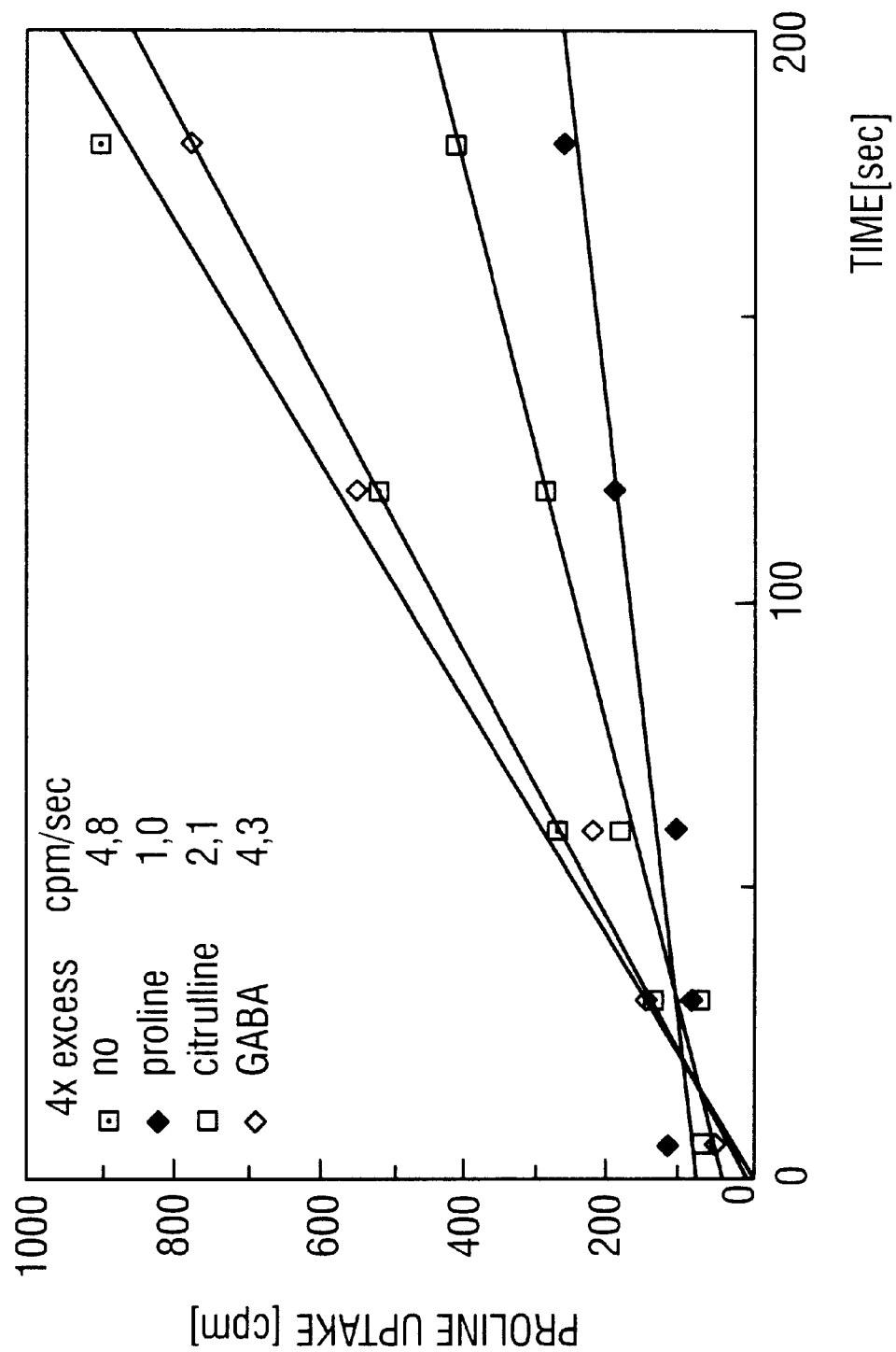
FIG. 2 shows the uptake of $^{14}$C-proline from the medium.

The yeast lines 22574d::PPP1-20 and 22574d::AAP2 that were obtained in a similar manner to Example 1 were grown in liquid medium until the culture reached the logarithmic phase. After centrifuging the culture, the cells are washed and taken up in 100 mm tris/HCl pH 4.5, 2 mM $MgCl_2$ and 0.6M sorbitol. Around 100 μL of the suspension was added to a solution of 0.5 mM L-proline plus 1 μCi $^{14}C$ labeled L-proline in 100 μL of the same buffer. The uptake of the labeled amino acid was measured by the process described by Cirillo (1989, Meth Enzymol 174: 617–622). The uptake of the labeled amino acid was compared, on the one hand, in co-incubation with protein modifying substance diethyl pyrocarbonate which is an inhibitor of the amino acid transport in membrane vesicles from *Beta vulgaris*, and, on the other hand, in co-incubation with other protein modifying substances. The calculated reduction is shown in Tables I and/or III. A competition experiment in which the specificity of the transporter could be read off with various amino acids and analogues is shown in Table II for PPP1-20 and in FIG. 4 for AAP2. An analogous experiment in which a competition for histidine uptake in the line JT16::AAP2 was tested is described in Example 5. The time period for PPP1-20 is shown in FIG. 2.

EXAMPLE 4

Transformation of Plants with a Construct for Overexpression of the Coding Region of Amino Acid Transporters From the plasmid pPPP1-20 that contains the cDNA for the amino acid transporter from Arabidopsis, an internal fragment of the insert was isolated after BamHI cleavage and cloned in the BamHI cleavage position from pAJ that was first linearized with the enzyme BamHI. Then the cDNA was prepared as the EcoRI/HindIII fragment from pA7 and cloned in the vector pBIN-HYG. After transformation by Agrobacteria, this was inserted for infection of leaf segments of tobacco and potato.

Ten independently obtained transformands in which the presence of the intact non-rearranged chimeric gene was demonstrated using Southern blot analysis were tested for modifications of amino acid and nitrogen content. Besides this, amino acid synthesis, photosynthesis rate and transportation were tested.

EXAMPLE 5

Studies in the Uptake of $^{14}C$-labeled Histidine in the Yeast Line AAP2

The yeast line JT16::AAP2, obtained in a similar manner to Example 1, was grown in liquid medium until the culture reached the logarithmic phase. After centrifuging the culture, the cells were washed and taken up in 10 mm tris/HCl pH 4.5, 2 mm $MgCl_2$ and 0.6M sorbitol. Around 100 ml of the suspension was added to a solution of 0.5 mm L-histidine plus 1 μCi $^{14}C$-labeled L-histidine in 100 μL of the same buffer. The uptake of the labeled amino acid was measured according to the method described by von Cirillo (1989, Meth Enzymol 174: 617–622). The uptake of the labeled amino acid was compared in a competition experiment with that from different amino acids and analogues in tenfold excess. The relationships are shown in FIG. 5.

TABLE I

Inhibition of the amino acid transport in 22574d::PPP1-20 - yeast strains by protein modifying substances

| | % of transport without inhibitor |
|---|---|
| 0.1 mM DEPC (diethyl pyrocarbonate) | 65 |
| 10 μM CCCP (Carbonyl cyanide m-chlorophenylhydrazone) | <3 |
| 10 μM 2, 4 DNP (Dinitrophenol) | |
| 1 mM sodium arsenate | 35 |
| 10 μM antimycin A | 29 |
| 500 μM PCMBS (p-chloromercuribenzenesulfonic acid) | 78 |

TABLE II

Competition by one, fourfold and tenfold excess of amino acids and analogues in 22574d::PPP1-20 - yeast strain

| Excess % remaining transport activity: | 1 x | 4 x | 10 x |
|---|---|---|---|
| glutamic acid | 64 | 27 | 30 |
| aspartic acid | 78 | | 27 |
| lysine | 86 | | 83 |
| histidine | 81 | 79 | 58 |
| arginine | 85 | 88 | 74 |
| threonine | — | 50 | — |
| L-proline | 49 | 21 | 14 |
| D-proline | 98 | | 95 |
| 3,4-di-OH proline | 86 | | 49 |
| azetidine-2-carboxylic acid | 91 | | 48 |
| OH-proline | 81 | | 45 |
| valine | — | 77 | 47 |
| isoleucine | — | 67 | — |
| asparagine | 64 | | 57 |
| glutamine | — | 27 | — |
| serine | 53 | | 18 |
| cysteine | — | 21 | — |
| methionine | 28 | | 8 |
| glycine | 69 | | 16 |
| alanine | 55 | 29 | 23 |
| leucine | — | | — |
| tyrosine | — | | — |
| tryptophan | 82 | 71 | 48 |
| phenylalanine | 45 | | 16 |
| citrulline | | 44 | |
| gamma-aminobutyric acid | | 90 | |

TABLE III

Inhibition of the amino acid transports in JT16::AAP2-yeast strain by protein modifying substances

| | % of transport without inhibitor |
|---|---|
| 1 mM DEPC (Diethyl pyrocarbonate) | 3.1 ± 1.6 |
| 10 μM CCCP (Carbonyl cyanide m-chlorophenylhydrazone) | 15.6 ± 2.1 |
| 10 μM 2,4 DNP (Dinitrophenol) | 7.6 ± 1.6 |

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. An isolated DNA molecule comprising a nucleotide sequence encoding an Arabidopsis amino acid transporter for membrane transport.

2. An isolated DNA molecule comprising a nucleotide sequence encoding an Arabidopsis amino acid transporter for membrane transport which complements a yeast amino acid transport mutation.

3. The isolated DNA molecule of claim 2 wherein the yeast has a proline transport mutation or a histidine synthesis and transport mutation.

4. A plasmid comprising the isolated DNA molecule of claim 1.

5. The plasmid of claim 4 further comprising a promoter operably linked to the isolated DNA molecule.

6. The plasmid of claim 4 further comprising a transcriptional termination sequence operably linked to the isolated DNA molecule.

7. The plasmid of claim 5 further comprising a transcriptional termination sequence operably linked to the isolated DNA molecule.

8. The plasmid of claim 4 wherein the isolated DNA molecule is in the sense orientation.

9. The plasmid of claim 4 wherein the isolated DNA molecule is in the anti-sense orientation.

10. A method for producing a transformed host cell comprising transforming a host cell with the isolated DNA molecule of claim 1.

11. A method for producing a transformed host cell comprising transforming a host cell with the plasmid of claim 4.

12. A method for producing a host cell having an increased amount of an amino acid transporter relative to a non-transformed cell comprising transforming a host the cell with the plasmid of claim 8.

13. A method for producing a host cell having a decreased amount of an amino acid transporter relative to a non-transformed cell comprising transforming a host cell with the plasmid of claim 9.

14. A method for altering the transport of metabolites in a host cell comprising transforming a host cell with the isolated DNA molecule of claim 1.

15. A cell obtained from the method of any one of claims 10, 11, 12, 13 or 14.

16. A bacterium comprising the isolated DNA molecule of claim 1.

17. A bacterium comprising the plasmid of claim 4.

18. A yeast strain comprising the isolated DNA molecule of claim 1.

19. A method for producing a plant comprising transfonning plant cells with the isolated DNA molecule of claim 1, and regenerating a transformed plant from the plant cells.

20. The method of claim 19 wherein the isolated DNA molecule is in the anti-sense orientation and the transformed plant has a decreased amount of amino acid transporter relative to a non-transformed plant.

21. The method of claim 19 wherein the isolated DNA molecule is in the sense orientation and the transformed plant has an increased amount of amino acid transporter relative to a non-transformed plant.

22. A plant obtained from the method of claim 19, 20 or 21.

23. A transgenic plant transformed so as to contain the isolated DNA molecule of claim 1 wherein said plant has an altered amount of Arabidopsis amino acid transporter activity relative to a non-transformed plant.

24. A transgenic plant comprising cells comprising the isolated DNA molecule of claim 1.

25. A transgenic plant having an altered amount of amino acid transporter activity by having been transformed so as to include at least one copy of the isolated DNA molecule of claim 1.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1685 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Arabidopsis thaliano (ix) FEATURE:
      (A) NAME/KEY: CDS
      (B) LOCATION: 57..1511
      (D) OTHER INFORMATION: /note= "amino acid transporter"

(xi) SEQUENCE DESCRIPTION: SEQ ID NO: 1:

```
CTTAAAACAT TTATTTTATC TTCTTCTTGT TCTCTCTTTC TCTTTCTCTC ATCACT                          56

ATG AAG AGT TTC AAC ACA GAA GGA CAC AAC CAC TCC ACG GCG GAA TCC                       104
Met Lys Ser Phe Asn Thr Glu Gly His Asn His Ser Thr Ala Glu Ser
 1               5                  10                  15

GGC GAT GCC TAC ACC GTG TCG GAC CCG ACA AAG AAC GTC GAT GAA GAT                       152
Gly Asp Ala Tyr Thr Val Ser Asp Pro Thr Lys Asn Val Asp Glu Asp
                20                  25                  30

GGT CGA GAG AAG CGT ACC GGG ACG TGG CTT ACG GCG AGT GCG CAT ATT                       200
Gly Arg Glu Lys Arg Thr Gly Thr Trp Leu Thr Ala Ser Ala His Ile
            35                  40                  45

ATC ACG GCG GTG ATA GGC TCC GGA GTG TTG TCT TTA GCA TGG GCT ATA                       248
Ile Thr Ala Val Ile Gly Ser Gly Val Leu Ser Leu Ala Trp Ala Ile
        50                  55                  60

GCT CAG CTT GGT TGG ATC GCA GGG ACA TCG ATC TTA CTC ATT TTC TCG                       296
Ala Gln Leu Gly Trp Ile Ala Gly Thr Ser Ile Leu Leu Ile Phe Ser
 65                  70                  75                  80

TTC ATT ACT TAC TTC ACC TCC ACC ATG CTT GCC GAT TGC TAC CGT GCG                       344
Phe Ile Thr Tyr Phe Thr Ser Thr Met Leu Ala Asp Cys Tyr Arg Ala
                 85                  90                  95

CCG GAT CCC GTC ACC GGA AAA CGG AAT TAC ACT TAC ATG GAC GTT GTT                       392
Pro Asp Pro Val Thr Gly Lys Arg Asn Tyr Thr Tyr Met Asp Val Val
                100                 105                 110

CGA TCT TAC CTC GGT GGT AGG AAA GTG CAG CTC TGT GGA GTG GCA CAA                       440
Arg Ser Tyr Leu Gly Gly Arg Lys Val Gln Leu Cys Gly Val Ala Gln
            115                 120                 125

TAT GGG AAT CTG ATT GGG GTC ACT GTT GGT TAC ACC ATC ACT GCT TCT                       488
Tyr Gly Asn Leu Ile Gly Val Thr Val Gly Tyr Thr Ile Thr Ala Ser
        130                 135                 140

ATT AGT TTG GTA GCG GTA GGG AAA TCG AAC TGC TTC CAC GAT AAA GGG                       536
Ile Ser Leu Val Ala Val Gly Lys Ser Asn Cys Phe His Asp Lys Gly
145                 150                 155                 160

CAC ACT GCG GAT TGT ACT ATA TCG AAT TAT CCG TAT ATG GCG GTT TTT                       584
His Thr Ala Asp Cys Thr Ile Ser Asn Tyr Pro Tyr Met Ala Val Phe
                165                 170                 175

GGT ATC ATT CAA GTT ATT CTT AGC CAG ATC CCA AAT TTC CAC AAG CTC                       632
Gly Ile Ile Gln Val Ile Leu Ser Gln Ile Pro Asn Phe His Lys Leu
                180                 185                 190

TCT TTT CTT TCC ATT ATG GCC GCA GTC ATG TCC TTT ACT TAT GCA ACT                       680
```

```
Ser Phe Leu Ser Ile Met Ala Ala Val Met Ser Phe Thr Tyr Ala Thr
        195                 200                 205

ATT GGA ATC GGT CTA GCC ATC GCA ACC GTC GCA GGT GGG AAA GTG GGT        728
Ile Gly Ile Gly Leu Ala Ile Ala Thr Val Ala Gly Gly Lys Val Gly
    210                 215                 220

AAG ACG AGT ATG ACG GGC ACA GCG GTT GGA GTA GAT GTA ACC GCA GCT        776
Lys Thr Ser Met Thr Gly Thr Ala Val Gly Val Asp Val Thr Ala Ala
225                 230                 235                 240

CAA AAG ATA TGG AGA TCG TTT CAA GCG GTT GGG GAC ATA GCG TTC GCC        824
Gln Lys Ile Trp Arg Ser Phe Gln Ala Val Gly Asp Ile Ala Phe Ala
                245                 250                 255

TAT GCT TAT GCC ACG GTT CTC ATC GAG ATT CAG GAT ACA CTA AGA TCT        872
Tyr Ala Tyr Ala Thr Val Leu Ile Glu Ile Gln Asp Thr Leu Arg Ser
            260                 265                 270

AGC CCA GCT GAG AAC AAA GCC ATG AAA AGA GCA AGT CTT GTG GGA GTA        920
Ser Pro Ala Glu Asn Lys Ala Met Lys Arg Ala Ser Leu Val Gly Val
        275                 280                 285

TCA ACC ACC ACT TTT TTC TAC ATC TTA TGT GGA TGC ATC GGC TAT GCT        968
Ser Thr Thr Thr Phe Phe Tyr Ile Leu Cys Gly Cys Ile Gly Tyr Ala
    290                 295                 300

GCA TTT GGA AAC AAT GCC CCT GGA GAT TTC CTC ACA GAT TTC GGG TTT       1016
Ala Phe Gly Asn Asn Ala Pro Gly Asp Phe Leu Thr Asp Phe Gly Phe
305                 310                 315                 320

TTC GAG CCC TTT TGG CTC ATT GAC TTT GCA AAC GCT TGC ATC GCT GTC       1064
Phe Glu Pro Phe Trp Leu Ile Asp Phe Ala Asn Ala Cys Ile Ala Val
                325                 330                 335

CAC CTT ATT GGT GCC TAT CAG GTG TTC GCG CAG CCG ATA TTC CAG TTT       1112
His Leu Ile Gly Ala Tyr Gln Val Phe Ala Gln Pro Ile Phe Gln Phe
            340                 345                 350

GTT GAG AAA AAA TGC AAC AGA AAC TAT CCA GAC AAC AAG TTC ATC ACT       1160
Val Glu Lys Lys Cys Asn Arg Asn Tyr Pro Asp Asn Lys Phe Ile Thr
        355                 360                 365

TCT GAA TAT TCA GTA AAC GTA CCT TTC CTT GGA AAA TTC AAC ATT AGC       1208
Ser Glu Tyr Ser Val Asn Val Pro Phe Leu Gly Lys Phe Asn Ile Ser
    370                 375                 380

CTC TTC AGA TTG GTG TGG AGG ACA GCT TAT GTG GTT ATA ACC ACT GTT       1256
Leu Phe Arg Leu Val Trp Arg Thr Ala Tyr Val Val Ile Thr Thr Val
385                 390                 395                 400

GTA GCT ATG ATA TTC CCT TTC TTC AAC GCG ATC TTA GGT CTT ATC GGA       1304
Val Ala Met Ile Phe Pro Phe Phe Asn Ala Ile Leu Gly Leu Ile Gly
                405                 410                 415

GCA GCT TCC TTC TGG CCT TTA ACG GTT TAT TTC CCT GTG GAG ATG CAC       1352
Ala Ala Ser Phe Trp Pro Leu Thr Val Tyr Phe Pro Val Glu Met His
            420                 425                 430

ATT GCA CAA ACC AAG ATT AAG AAG TAC TCT GCT AGA TGG ATT GCG CTG       1400
Ile Ala Gln Thr Lys Ile Lys Lys Tyr Ser Ala Arg Trp Ile Ala Leu
        435                 440                 445

AAA ACG ATG TGC TAT GTT TGC TTG ATC GTC TCG CTC TTA GCT GCA GCC       1448
Lys Thr Met Cys Tyr Val Cys Leu Ile Val Ser Leu Leu Ala Ala Ala
    450                 455                 460

GGA TCC ATC GCA GGA CTT ATA AGT AGT GTC AAA ACC TAC AAG CCC TTC       1496
Gly Ser Ile Ala Gly Leu Ile Ser Ser Val Lys Thr Tyr Lys Pro Phe
465                 470                 475                 480

CGG ACT ATG CAT GAG TGAGTTTGAG ATCCTCAAGA GAGTCAAAAA TATATGTAGT       1551
Arg Thr Met His Glu
                485

AGTTTGGTCT TTCTGTTAAA CTATCTGGTG TCTAAATCCA ATGAGAATGC TTTATTGCTA     1611

AAACTTCATG AATCTCTCTG TATCTACATC TTTCAATCTA ATACATATGA GCTCTTCCAA     1671
```

AAAAAAAAAA AAAA                                                          1685

(2) INFORMATION FOR SEQ ID NO: 2:

(i) SEQUENCE CHARACTERISTICS:
        (A) LENGTH: 485 amino acids
        (B) TYPE: amino acid
        (D) TOPOLOGY: linear (ii) MOLECULE TYPE: protein (xi) SEQUENCE DESCRIPTION: SEQ ID NO: 2:

Met Lys Ser Phe Asn Thr Glu Gly His Asn His Ser Thr Ala Glu Ser
 1               5                  10                  15

Gly Asp Ala Tyr Thr Val Ser Asp Pro Thr Lys Asn Val Asp Glu Asp
            20                  25                  30

Gly Arg Glu Lys Arg Thr Gly Thr Trp Leu Thr Ala Ser Ala His Ile
        35                  40                  45

Ile Thr Ala Val Ile Gly Ser Gly Val Leu Ser Leu Ala Trp Ala Ile
 50                  55                  60

Ala Gln Leu Gly Trp Ile Ala Gly Thr Ser Ile Leu Leu Ile Phe Ser
 65                  70                  75                  80

Phe Ile Thr Tyr Phe Thr Ser Thr Met Leu Ala Asp Cys Tyr Arg Ala
                85                  90                  95

Pro Asp Pro Val Thr Gly Lys Arg Asn Tyr Thr Tyr Met Asp Val Val
            100                 105                 110

Arg Ser Tyr Leu Gly Gly Arg Lys Val Gln Leu Cys Gly Val Ala Gln
        115                 120                 125

Tyr Gly Asn Leu Ile Gly Val Thr Val Gly Tyr Thr Ile Thr Ala Ser
    130                 135                 140

Ile Ser Leu Val Ala Val Gly Lys Ser Asn Cys Phe His Asp Lys Gly
145                 150                 155                 160

His Thr Ala Asp Cys Thr Ile Ser Asn Tyr Pro Tyr Met Ala Val Phe
                165                 170                 175

Gly Ile Ile Gln Val Ile Leu Ser Gln Ile Pro Asn Phe His Lys Leu
            180                 185                 190

Ser Phe Leu Ser Ile Met Ala Ala Val Met Ser Phe Thr Tyr Ala Thr
        195                 200                 205

Ile Gly Ile Gly Leu Ala Ile Ala Thr Val Ala Gly Gly Lys Val Gly
    210                 215                 220

Lys Thr Ser Met Thr Gly Thr Ala Val Gly Val Asp Val Thr Ala Ala
225                 230                 235                 240

Gln Lys Ile Trp Arg Ser Phe Gln Ala Val Gly Asp Ile Ala Phe Ala
                245                 250                 255

Tyr Ala Tyr Ala Thr Val Leu Ile Glu Ile Gln Asp Thr Leu Arg Ser
            260                 265                 270

Ser Pro Ala Glu Asn Lys Ala Met Lys Arg Ala Ser Leu Val Gly Val
        275                 280                 285

Ser Thr Thr Thr Phe Phe Tyr Ile Leu Cys Gly Cys Ile Gly Tyr Ala
    290                 295                 300

Ala Phe Gly Asn Asn Ala Pro Gly Asp Phe Leu Thr Asp Phe Gly Phe
305                 310                 315                 320

Phe Glu Pro Phe Trp Leu Ile Asp Phe Ala Asn Ala Cys Ile Ala Val
                325                 330                 335

His Leu Ile Gly Ala Tyr Gln Val Phe Ala Gln Pro Ile Phe Gln Phe
            340                 345                 350

```
Val Glu Lys Lys Cys Asn Arg Asn Tyr Pro Asp Asn Lys Phe Ile Thr
        355                 360                 365

Ser Glu Tyr Ser Val Asn Val Pro Phe Leu Gly Lys Phe Asn Ile Ser
    370                 375                 380

Leu Phe Arg Leu Val Trp Arg Thr Ala Tyr Val Val Ile Thr Thr Val
385                 390                 395                 400

Val Ala Met Ile Phe Pro Phe Asn Ala Ile Leu Gly Leu Ile Gly
                405                 410                 415

Ala Ala Ser Phe Trp Pro Leu Thr Val Tyr Phe Pro Val Glu Met His
            420                 425                 430

Ile Ala Gln Thr Lys Ile Lys Lys Tyr Ser Ala Arg Trp Ile Ala Leu
        435                 440                 445

Lys Thr Met Cys Tyr Val Cys Leu Ile Val Ser Leu Leu Ala Ala Ala
    450                 455                 460

Gly Ser Ile Ala Gly Leu Ile Ser Ser Val Lys Thr Tyr Lys Pro Phe
465                 470                 475                 480

Arg Thr Met His Glu
            485
```

(2) INFORMATION FOR SEQ ID NO: 3:

(i) SEQUENCE CHARACTERISTICS:
        (A) LENGTH: 1740 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Arabidopsis thaliana (ix) FEATURE:
        (A) NAME/KEY: CDS
        (B) LOCATION: 80..1558
        (D) OTHER INFORMATION: /product= "amino acid transporter"

(xi) SEQUENCE DESCRIPTION: SEQ ID NO: 3:

```
CTATTTTATA ATTCCTCTTC TTTTTGTTCA TAGCTTTGTA ATTATAGTCT TATTTCTCTT    60

TAAGGCTCAA TAAGAGGAG ATG GGT GAA ACC GCT GCC GCC AAT AAC CAC CGT    112
                    Met Gly Glu Thr Ala Ala Ala Asn Asn His Arg
                     1               5                  10

CAC CAC CAC CAT CAC GGC CAC CAG GTC TTT GAC GTG GCC AGC CAC GAT    160
His His His His His Gly His Gln Val Phe Asp Val Ala Ser His Asp
                15                  20                  25

TTC GTC CCT CCA CAA CCG GCT TTT AAA TGC TTC GAT GAT GAT GGC CGC    208
Phe Val Pro Pro Gln Pro Ala Phe Lys Cys Phe Asp Asp Asp Gly Arg
            30                  35                  40

CTC AAA AGA ACT GGG ACT GTT TGG ACC GCG AGC GCT CAT ATA ATA ACT    256
Leu Lys Arg Thr Gly Thr Val Trp Thr Ala Ser Ala His Ile Ile Thr
        45                  50                  55

GCG GTT ATC GGA TCC GGC GTT TTG TCA TTG GCG TGG GCG ATT GCA CAG    304
Ala Val Ile Gly Ser Gly Val Leu Ser Leu Ala Trp Ala Ile Ala Gln
60                  65                  70                  75

CTC GGA TGG ATC GCT GGC CCT GCT GTG ATG CTA TTG TTC TCT CTT GTT    352
Leu Gly Trp Ile Ala Gly Pro Ala Val Met Leu Leu Phe Ser Leu Val
                80                  85                  90

ACT CTT TAC TCC TCC ACA CTT CTT AGC GAC TGC TAC AGA ACC GGC GAT    400
Thr Leu Tyr Ser Ser Thr Leu Leu Ser Asp Cys Tyr Arg Thr Gly Asp
            95                  100                 105
```

```
GCA GTG TCT GGC AAG AGA AAC TAC ACT TAC ATG GAT GCC GTT CGA TCA      448
Ala Val Ser Gly Lys Arg Asn Tyr Thr Tyr Met Asp Ala Val Arg Ser
        110                 115                 120

ATT CTC GGT GGG TTC AAG TTC AAG ATT TGT GGG TTG ATT CAA TAC TTG      496
Ile Leu Gly Gly Phe Lys Phe Lys Ile Cys Gly Leu Ile Gln Tyr Leu
125                 130                 135

AAT CTC TTT GGT ATC GCA ATT GGA TAC ACG ATA GCA GCT TCC ATA AGC      544
Asn Leu Phe Gly Ile Ala Ile Gly Tyr Thr Ile Ala Ala Ser Ile Ser
140                 145                 150                 155

ATG ATG GCG ATC AAG AGA TCC AAC TGC TTC CAC AAG AGT GGA GGA AAA      592
Met Met Ala Ile Lys Arg Ser Asn Cys Phe His Lys Ser Gly Gly Lys
        160                 165                 170

GAC CCA TGT CAC ATG TCC AGT AAT CCT TAC ATG ATC GTA TTT GGT GTG      640
Asp Pro Cys His Met Ser Ser Asn Pro Tyr Met Ile Val Phe Gly Val
            175                 180                 185

GCA GAG ATC TTG CTC TCT CAG GTT CCT GAT TTC GAT CAG ATT TGG TGG      688
Ala Glu Ile Leu Leu Ser Gln Val Pro Asp Phe Asp Gln Ile Trp Trp
        190                 195                 200

ATC TCC ATT GTT GCA GCT GTT ATG TCC TTC ACT TAC TCT GCC ATT GGT      736
Ile Ser Ile Val Ala Ala Val Met Ser Phe Thr Tyr Ser Ala Ile Gly
205                 210                 215

CTA GCT CTT GGA ATC GTT CAA GTT GCA GCG AAT GGA GTT TTC AAA GGA      784
Leu Ala Leu Gly Ile Val Gln Val Ala Ala Asn Gly Val Phe Lys Gly
220                 225                 230                 235

AGT CTC ACT GGA ATA AGC ATC GGA ACA GTG ACT CAA ACA CAG AAG ATA      832
Ser Leu Thr Gly Ile Ser Ile Gly Thr Val Thr Gln Thr Gln Lys Ile
        240                 245                 250

TGG AGA ACC TTC CAA GCA CTT GGA GAC ATT GCC TTT GCG TAC TCA TAC      880
Trp Arg Thr Phe Gln Ala Leu Gly Asp Ile Ala Phe Ala Tyr Ser Tyr
        255                 260                 265

TCT GTT GTC CTA ATC GAG ATT CAG GAT ACT GTA AGA TCC CCA CCG GCG      928
Ser Val Val Leu Ile Glu Ile Gln Asp Thr Val Arg Ser Pro Pro Ala
        270                 275                 280

GAA TCG AAA ACG ATG AAG AAA GCA ACA AAA ATC AGT ATT GCC GTC ACA      976
Glu Ser Lys Thr Met Lys Lys Ala Thr Lys Ile Ser Ile Ala Val Thr
285                 290                 295

ACT ATC TTC TAC ATG CTA TGT GGC TCA ATG GGT TAT GCC GCT TTT GGA     1024
Thr Ile Phe Tyr Met Leu Cys Gly Ser Met Gly Tyr Ala Ala Phe Gly
300                 305                 310                 315

GAT GCA GCA CCG GGA AAC CTC CTC ACC GGT TTT GGA TTC TAC AAC CCG     1072
Asp Ala Ala Pro Gly Asn Leu Leu Thr Gly Phe Gly Phe Tyr Asn Pro
            320                 325                 330

TTT TGG CTC CTT GAC ATA GCT AAC GCC GCC ATT GTT GTC CAC CTC GTT     1120
Phe Trp Leu Leu Asp Ile Ala Asn Ala Ala Ile Val Val His Leu Val
        335                 340                 345

GGA GCT TAC CAA GTC TTT GCT CAG CCC ATC TTT GCC TTT ATT GAA AAA     1168
Gly Ala Tyr Gln Val Phe Ala Gln Pro Ile Phe Ala Phe Ile Glu Lys
        350                 355                 360

TCA GTC GCA GAG AGA TAT CCA GAC AAT GAC TTC CTC AGC AAG GAA TTT     1216
Ser Val Ala Glu Arg Tyr Pro Asp Asn Asp Phe Leu Ser Lys Glu Phe
365                 370                 375

GAA ATC AGA ATC CCC GGA TTT AAG TCT CCT TAC AAA GTA AAC GTT TTC     1264
Glu Ile Arg Ile Pro Gly Phe Lys Ser Pro Tyr Lys Val Asn Val Phe
380                 385                 390                 395

AGG ATG GTT TAC AGG AGT GGC TTT GTC GTT ACA ACC ACC GTG ATA TCG     1312
Arg Met Val Tyr Arg Ser Gly Phe Val Val Thr Thr Thr Val Ile Ser
        400                 405                 410

ATG CTG ATG CCG TTT TTT AAC GAC GTG GTC GGG ATC TTA GGG GCG TTA     1360
Met Leu Met Pro Phe Phe Asn Asp Val Val Gly Ile Leu Gly Ala Leu
        415                 420                 425
```

```
GGG TTT TGG CCC TTG ACG GTT TAT TTT CCG GTG GAG ATG TAT ATT AAG      1408
Gly Phe Trp Pro Leu Thr Val Tyr Phe Pro Val Glu Met Tyr Ile Lys
            430                 435                 440

CAG AGG AAG GTT GAG AAA TGG AGC ACG AGA TGG GTG TGT TTA CAG ATG      1456
Gln Arg Lys Val Glu Lys Trp Ser Thr Arg Trp Val Cys Leu Gln Met
            445                 450                 455

CTT AGT GTT GCT TGT CTT GTG ATC TCG GTG GTC GCC GGG GTT GGA TCA      1504
Leu Ser Val Ala Cys Leu Val Ile Ser Val Val Ala Gly Val Gly Ser
460                 465                 470                 475

ATC GCC GGA GTG ATG CTT GAT CTT AAG GTC TAT AAG CCA TTC AAG TCT      1552
Ile Ala Gly Val Met Leu Asp Leu Lys Val Tyr Lys Pro Phe Lys Ser
                480                 485                 490

ACA TAT TGATGATTAT GGACCATGAA CAACAGAGAG AGTTGGTGTG TAAAGTTTAC       1608
Thr Tyr
CATTTCAAAG AAAACTCCAA AAATGTGTAT ATTGTATGTT GTTCTCATTT CGTATGGTCT    1668

CATCTTTGTA ATAAAATTTA AAACTTATGT TATAAATTAT AAAAAAAAAA AAAAAAAAAA    1728

AAAAAAAAAA AA                                                        1740

(2) INFORMATION FOR SEQ ID NO: 4:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO: 4:

Met Gly Glu Thr Ala Ala Ala Asn Asn His Arg His His His His
1               5                   10                  15

Gly His Gln Val Phe Asp Val Ala Ser His Asp Phe Val Pro Pro Gln
                20                  25                  30

Pro Ala Phe Lys Cys Phe Asp Asp Gly Arg Leu Lys Arg Thr Gly
            35                  40                  45

Thr Val Trp Thr Ala Ser Ala His Ile Ile Thr Ala Val Ile Gly Ser
    50                  55                  60

Gly Val Leu Ser Leu Ala Trp Ala Ile Ala Gln Leu Gly Trp Ile Ala
65                  70                  75                  80

Gly Pro Ala Val Met Leu Leu Phe Ser Leu Val Thr Leu Tyr Ser Ser
                85                  90                  95

Thr Leu Leu Ser Asp Cys Tyr Arg Thr Gly Asp Ala Val Ser Gly Lys
            100                 105                 110

Arg Asn Tyr Thr Tyr Met Asp Ala Val Arg Ser Ile Leu Gly Gly Phe
        115                 120                 125

Lys Phe Lys Ile Cys Gly Leu Ile Gln Tyr Leu Asn Leu Phe Gly Ile
130                 135                 140

Ala Ile Gly Tyr Thr Ile Ala Ala Ser Ile Ser Met Met Ala Ile Lys
145                 150                 155                 160

Arg Ser Asn Cys Phe His Lys Ser Gly Gly Lys Asp Pro Cys His Met
            165                 170                 175

Ser Ser Asn Pro Tyr Met Ile Val Phe Gly Val Ala Glu Ile Leu Leu
        180                 185                 190

Ser Gln Val Pro Asp Phe Asp Gln Ile Trp Trp Ile Ser Ile Val Ala
    195                 200                 205

Ala Val Met Ser Phe Thr Tyr Ser Ala Ile Gly Leu Ala Leu Gly Ile
210                 215                 220
```

-continued

```
Val Gln Val Ala Ala Asn Gly Val Phe Lys Gly Ser Leu Thr Gly Ile
225                 230                 235                 240

Ser Ile Gly Thr Val Thr Gln Thr Gln Lys Ile Trp Arg Thr Phe Gln
                245                 250                 255

Ala Leu Gly Asp Ile Ala Phe Ala Tyr Ser Tyr Ser Val Val Leu Ile
                260                 265                 270

Glu Ile Gln Asp Thr Val Arg Ser Pro Pro Ala Glu Ser Lys Thr Met
                275                 280                 285

Lys Lys Ala Thr Lys Ile Ser Ile Ala Val Thr Thr Ile Phe Tyr Met
                290                 295                 300

Leu Cys Gly Ser Met Gly Tyr Ala Ala Phe Gly Asp Ala Ala Pro Gly
305                 310                 315                 320

Asn Leu Leu Thr Gly Phe Gly Phe Tyr Asn Pro Phe Trp Leu Leu Asp
                325                 330                 335

Ile Ala Asn Ala Ala Ile Val Val His Leu Val Gly Ala Tyr Gln Val
                340                 345                 350

Phe Ala Gln Pro Ile Phe Ala Phe Ile Glu Lys Ser Val Ala Glu Arg
                355                 360                 365

Tyr Pro Asp Asn Asp Phe Leu Ser Lys Glu Phe Glu Ile Arg Ile Pro
    370                 375                 380

Gly Phe Lys Ser Pro Tyr Lys Val Asn Val Phe Arg Met Val Tyr Arg
385                 390                 395                 400

Ser Gly Phe Val Val Thr Thr Thr Val Ile Ser Met Leu Met Pro Phe
                405                 410                 415

Phe Asn Asp Val Val Gly Ile Leu Gly Ala Leu Gly Phe Trp Pro Leu
                420                 425                 430

Thr Val Tyr Phe Pro Val Glu Met Tyr Ile Lys Gln Arg Lys Val Glu
            435                 440                 445

Lys Trp Ser Thr Arg Trp Val Cys Leu Gln Met Leu Ser Val Ala Cys
    450                 455                 460

Leu Val Ile Ser Val Val Ala Gly Val Gly Ser Ile Ala Gly Val Met
465                 470                 475                 480

Leu Asp Leu Lys Val Tyr Lys Pro Phe Lys Ser Thr Tyr
                485                 490
```